United States Patent
Frey et al.

(10) Patent No.: US 10,743,890 B2
(45) Date of Patent: Aug. 18, 2020

(54) DRILL APPARATUS AND SURGICAL FIXATION DEVICES AND METHODS FOR USING THE SAME

(71) Applicant: Mighty Oak Medical, Inc., Englewood, CO (US)

(72) Inventors: George Frey, Englewood, CO (US); Sean Starkman, Littleton, CO (US)

(73) Assignee: MIGHTY OAK MEDICAL, INC., Englewood, CO (US)

( * ) Notice: Subject to any disclaimer, the term of this patent is extended or adjusted under 35 U.S.C. 154(b) by 512 days.

(21) Appl. No.: 15/675,378

(22) Filed: Aug. 11, 2017

(65) Prior Publication Data
US 2018/0042619 A1 Feb. 15, 2018

Related U.S. Application Data

(63) Continuation-in-part of application No. 15/416,975, filed on Jan. 26, 2017, now Pat. No. 9,987,024.
(Continued)

(51) Int. Cl.
*A61B 17/16* (2006.01)
*A61B 17/17* (2006.01)
(Continued)

(52) U.S. Cl.
CPC ........ *A61B 17/1626* (2013.01); *A61B 17/151* (2013.01); *A61B 17/1615* (2013.01); *A61B 17/1671* (2013.01); *A61B 17/1757* (2013.01); *A61B 34/00* (2016.02); *A61F 2/44* (2013.01); *A61F 2/4611* (2013.01); *G09B 23/30* (2013.01);
(Continued)

(58) Field of Classification Search
CPC ...... A61B 34/00; A61B 17/16; A61B 17/1615
See application file for complete search history.

(56) References Cited

U.S. PATENT DOCUMENTS

| 3,151,392 A | 10/1964 | Chambers |
| 5,092,866 A | 3/1992 | Breard et al. |

(Continued)

FOREIGN PATENT DOCUMENTS

| CA | 2736525 | 3/2010 |
| CA | 2862341 | 8/2013 |

(Continued)

OTHER PUBLICATIONS

"Calculator for Designing Compression Springs," eFunda, Inc., first published online Sep. 25, 2000 per Wayback Machine, 2 pages, [retrieved from: http://www.efunda.com/designstandards/springs/calc_comp_designer.cfm].

(Continued)

*Primary Examiner* — Andrew Yang
(74) *Attorney, Agent, or Firm* — FisherBroyles LLP; Ian R. Walsworth

(57) ABSTRACT

The present application relates to systems, methods, and devices for performing drilling operations, such as in a surgical setting. The embodiments disclosed herein include handheld drill apparatus configured to be used with guides for completing a specific operation. The drill apparatus is capable of receiving instructions either through programming, from a memory device, or from scanning a device located on an external item, such as a guide.

18 Claims, 17 Drawing Sheets

Related U.S. Application Data

(60) Provisional application No. 62/373,855, filed on Aug. 11, 2016.

(51) Int. Cl.

| | | |
|---|---|---|
| *A61B 17/15* | (2006.01) | |
| *G09B 23/30* | (2006.01) | |
| *A61F 2/46* | (2006.01) | |
| *A61F 2/44* | (2006.01) | |
| *A61B 34/00* | (2016.01) | |
| *A61B 17/00* | (2006.01) | |
| *A61B 17/34* | (2006.01) | |
| *A61B 90/00* | (2016.01) | |
| *A61F 2/30* | (2006.01) | |
| *A61B 17/56* | (2006.01) | |
| *A61B 34/10* | (2016.01) | |
| *A61B 34/20* | (2016.01) | |
| *B33Y 80/00* | (2015.01) | |
| *B33Y 10/00* | (2015.01) | |
| *A61B 90/98* | (2016.01) | |
| *A61B 90/96* | (2016.01) | |

(52) U.S. Cl.
CPC ............ *A61B 17/1622* (2013.01); *A61B 34/20* (2016.02); *A61B 34/25* (2016.02); *A61B 90/96* (2016.02); *A61B 90/98* (2016.02); *A61B 2017/00017* (2013.01); *A61B 2017/00123* (2013.01); *A61B 2017/00199* (2013.01); *A61B 2017/00398* (2013.01); *A61B 2017/00734* (2013.01); *A61B 2017/3447* (2013.01); *A61B 2017/568* (2013.01); *A61B 2034/107* (2016.02); *A61B 2090/061* (2016.02); *A61B 2090/067* (2016.02); *A61F 2/30965* (2013.01); *A61F 2/4405* (2013.01); *A61F 2002/30948* (2013.01); *A61F 2002/30952* (2013.01); *A61F 2002/4687* (2013.01); *A61F 2310/00017* (2013.01); *A61F 2310/00023* (2013.01); *A61F 2310/00029* (2013.01); *A61F 2310/00047* (2013.01); *A61F 2310/00059* (2013.01); *B33Y 10/00* (2014.12); *B33Y 80/00* (2014.12)

(56) References Cited

U.S. PATENT DOCUMENTS

| | | |
|---|---|---|
| 5,129,904 A | 7/1992 | Illi |
| 5,201,734 A | 4/1993 | Cozard et al. |
| 5,291,901 A | 3/1994 | Graf |
| 5,360,448 A | 11/1994 | Thramann |
| 5,387,213 A | 1/1995 | Breard et al. |
| D359,557 S | 6/1995 | Hayes |
| 5,490,409 A | 2/1996 | Weber |
| 5,527,312 A | 6/1996 | Ray |
| 5,562,737 A | 10/1996 | Graf |
| 5,569,246 A | 10/1996 | Ojima et al. |
| 5,591,233 A | 1/1997 | Kelman et al. |
| 5,725,581 A | 3/1998 | Branemark |
| D403,066 S | 12/1998 | DeFonzo |
| 5,865,846 A | 2/1999 | Bryan et al. |
| RE36,221 E | 6/1999 | Breard et al. |
| D412,032 S | 7/1999 | Mikula-Curtis et al. |
| 5,961,516 A | 10/1999 | Graf |
| 5,993,453 A | 11/1999 | Bullara et al. |
| 6,006,581 A | 12/1999 | Holmes |
| D420,132 S | 2/2000 | Bucholz et al. |
| 6,030,401 A | 2/2000 | Marino |
| 6,035,691 A | 3/2000 | Lin et al. |
| 6,048,343 A | 4/2000 | Mathis et al. |
| 6,063,088 A | 5/2000 | Winslow |
| D428,989 S | 8/2000 | Segemark et al. |
| 6,113,602 A | 9/2000 | Sand |
| 6,142,998 A | 11/2000 | Smith et al. |
| 6,221,077 B1 | 4/2001 | Rinner et al. |
| 6,290,724 B1 | 9/2001 | Marino |
| 6,309,395 B1 | 10/2001 | Smith et al. |
| 6,328,738 B1 | 12/2001 | Suddaby |
| 6,364,880 B1 | 4/2002 | Michelson |
| 6,402,750 B1 | 6/2002 | Atkinson et al. |
| 6,445,211 B1 | 9/2002 | Saripella |
| 6,644,087 B1 | 11/2003 | Ralph et al. |
| 6,663,633 B1 | 12/2003 | Pierson, III |
| 6,711,432 B1 | 3/2004 | Krause et al. |
| 6,719,795 B1 | 4/2004 | Cornwall et al. |
| 6,755,839 B2 | 6/2004 | Van Hoeck et al. |
| 6,835,207 B2 | 12/2004 | Zacouto et al. |
| 7,014,640 B2 | 3/2006 | Kemppanien et al. |
| 7,025,769 B1 | 4/2006 | Ferree |
| 7,066,957 B2 | 6/2006 | Graf |
| 7,077,864 B2 | 7/2006 | Bryd, III et al. |
| D532,515 S | 11/2006 | Buttler et al. |
| D533,664 S | 12/2006 | Butler et al. |
| 7,207,992 B2 | 4/2007 | Ritland |
| 7,235,076 B2 | 6/2007 | Pacheco |
| 7,288,093 B2 | 10/2007 | Michelson |
| 7,291,150 B2 | 11/2007 | Graf |
| 7,341,590 B2 | 3/2008 | Ferree |
| 7,387,643 B2 | 6/2008 | Michelson |
| 7,406,775 B2 | 8/2008 | Funk et al. |
| 7,454,939 B2 | 11/2008 | Garner et al. |
| 7,491,180 B2 | 2/2009 | Pacheco |
| 7,537,664 B2 | 5/2009 | Oneill et al. |
| 7,559,931 B2 | 7/2009 | Stone |
| 7,578,851 B2 | 8/2009 | Dong et al. |
| 7,623,902 B2 | 11/2009 | Pacheco |
| D606,195 S | 12/2009 | Eisen et al. |
| 7,658,610 B2 | 2/2010 | Knopp |
| D618,796 S | 6/2010 | Cantu et al. |
| 7,844,356 B2 | 11/2010 | Matov et al. |
| 7,854,752 B2 | 12/2010 | Colleran et al. |
| 7,955,355 B2 | 6/2011 | Cin |
| 7,957,824 B2 | 6/2011 | Boronvinskih et al. |
| 7,957,831 B2 | 6/2011 | Isaacs |
| 7,967,868 B2 | 6/2011 | White et al. |
| 8,057,482 B2 | 11/2011 | Stone et al. |
| 8,070,752 B2 | 12/2011 | Metzger et al. |
| 8,092,465 B2 | 1/2012 | Metzger et al. |
| 8,118,815 B2 | 2/2012 | van der Walt |
| 8,159,753 B2 | 4/2012 | Ojeda et al. |
| 8,167,884 B2 | 5/2012 | Pacheco |
| 8,175,683 B2 | 5/2012 | Roose |
| 8,206,396 B2 | 6/2012 | Trabish |
| 8,214,014 B2 | 7/2012 | Pacheco |
| 8,236,006 B2 | 8/2012 | Hamada |
| 8,241,293 B2 | 8/2012 | Stone et al. |
| 8,257,083 B2 | 9/2012 | Berckmans et al. |
| D669,176 S | 10/2012 | Frey |
| D669,984 S | 10/2012 | Cheney et al. |
| 8,277,461 B2 | 10/2012 | Pacheco |
| 8,282,646 B2 | 10/2012 | Schoenefeld et al. |
| 8,292,967 B2 | 10/2012 | Brown et al. |
| 8,298,235 B2 | 10/2012 | Grinberg et al. |
| 8,298,237 B2 | 10/2012 | Schoenefeld et al. |
| 8,298,242 B2 | 10/2012 | Justis et al. |
| D672,038 S | 12/2012 | Frey |
| 8,323,322 B2 | 12/2012 | Dawson et al. |
| 8,357,111 B2 | 1/2013 | Caillouette et al. |
| 8,377,066 B2 | 2/2013 | Katrana et al. |
| 8,407,067 B2 | 3/2013 | Uthgenannt et al. |
| 8,419,740 B2 | 4/2013 | Aram et al. |
| D685,087 S | 6/2013 | Voic |
| 8,460,303 B2 | 6/2013 | Park |
| 8,475,505 B2 | 7/2013 | Nebosky et al. |
| 8,480,679 B2 | 7/2013 | Park et al. |
| 8,535,387 B2 | 9/2013 | Meridew et al. |
| 8,540,719 B2 | 9/2013 | Peukert et al. |
| 8,545,509 B2 | 10/2013 | Park et al. |
| 8,549,888 B2 | 10/2013 | Isaacs |
| 8,568,487 B2 | 10/2013 | Witt et al. |
| 8,591,516 B2 | 11/2013 | Metzger et al. |
| 8,603,180 B2 | 12/2013 | White et al. |

(56) References Cited

U.S. PATENT DOCUMENTS

| | | |
|---|---|---|
| 8,607,603 B2 | 12/2013 | Justis et al. |
| 8,608,748 B2 | 12/2013 | Metzger et al. |
| 8,608,749 B2 | 12/2013 | Meridew et al. |
| 8,632,547 B2 | 1/2014 | Maxson et al. |
| 8,668,700 B2 | 3/2014 | Catanzarite |
| 8,671,572 B2 | 3/2014 | Schlottig et al. |
| D705,929 S | 5/2014 | Frey |
| 8,721,651 B2 | 5/2014 | Loke et al. |
| 8,758,357 B2 | 6/2014 | Frey |
| 8,808,302 B2 | 8/2014 | Roose et al. |
| 8,808,303 B2 | 8/2014 | Stemniski et al. |
| 8,821,506 B2 | 9/2014 | Mitchell |
| 8,858,561 B2 | 10/2014 | White et al. |
| 8,864,769 B2 | 10/2014 | Stone et al. |
| 8,870,889 B2 | 10/2014 | Frey |
| D718,862 S | 12/2014 | Matheny |
| D718,863 S | 12/2014 | Matheny |
| D718,864 S | 12/2014 | Matheny |
| 8,900,279 B2 | 12/2014 | Assell et al. |
| 8,979,749 B2 | 3/2015 | Gorek et al. |
| 8,979,911 B2 | 3/2015 | Martineau et al. |
| 8,992,538 B2 | 3/2015 | Keefer |
| D726,914 S | 4/2015 | Matheny |
| 9,017,412 B2 | 4/2015 | Wolters et al. |
| 9,044,285 B2 | 6/2015 | Harper |
| 9,066,727 B2 | 6/2015 | Catanzarite et al. |
| 9,066,816 B2 | 6/2015 | Allard et al. |
| 9,113,971 B2 | 8/2015 | Metzger et al. |
| D738,498 S | 9/2015 | Frey et al. |
| 9,138,325 B2 | 9/2015 | Mouw |
| 9,173,661 B2 | 11/2015 | Metzger et al. |
| D745,671 S | 12/2015 | Frey et al. |
| D745,672 S | 12/2015 | Frey et al. |
| D745,673 S | 12/2015 | Frey et al. |
| 9,198,678 B2 | 12/2015 | Frey et al. |
| 9,216,045 B2 | 12/2015 | Martineau et al. |
| 9,451,973 B2 | 9/2016 | Heilman et al. |
| 9,456,901 B2 | 10/2016 | Jones et al. |
| D775,335 S | 12/2016 | Frey et al. |
| 9,642,633 B2 | 5/2017 | Frey et al. |
| 9,649,160 B2 | 5/2017 | van der Walt et al. |
| 9,662,157 B2 | 5/2017 | Schneider et al. |
| 9,675,400 B2 | 6/2017 | Katrana et al. |
| 9,737,339 B2 | 8/2017 | Copp et al. |
| 9,814,497 B1 | 11/2017 | Al-Habib et al. |
| 9,826,991 B2 | 11/2017 | Kaiser et al. |
| 9,839,448 B2 | 12/2017 | Reckling et al. |
| 9,848,922 B2 | 12/2017 | Tohmeh et al. |
| 9,913,669 B1 | 3/2018 | Scholl et al. |
| 9,949,843 B2 | 4/2018 | Reiley et al. |
| 9,968,408 B1 | 5/2018 | Casey et al. |
| 9,987,024 B2 | 6/2018 | Frey et al. |
| 10,085,784 B2 | 10/2018 | Ono et al. |
| 10,166,033 B2 | 1/2019 | Reiley et al. |
| 2004/0097925 A1 | 5/2004 | Boehm et al. |
| 2004/0144149 A1 | 7/2004 | Strippgen et al. |
| 2004/0243481 A1 | 12/2004 | Bradbury et al. |
| 2004/0267260 A1 | 12/2004 | Mack et al. |
| 2005/0085815 A1 | 4/2005 | Harms et al. |
| 2005/0148843 A1 | 7/2005 | Roose |
| 2005/0177156 A1 | 8/2005 | Timm et al. |
| 2005/0203514 A1 | 9/2005 | Jahng et al. |
| 2005/0203519 A1 | 9/2005 | Harms et al. |
| 2005/0262911 A1 | 12/2005 | Dankowicz et al. |
| 2005/0288672 A1 | 12/2005 | Ferree |
| 2006/0036323 A1 | 2/2006 | Carl et al. |
| 2006/0058792 A1 | 3/2006 | Hynes |
| 2006/0084986 A1 | 4/2006 | Grinberg et al. |
| 2006/0095044 A1 | 5/2006 | Grady, Jr. et al. |
| 2006/0149375 A1 | 7/2006 | Yuan et al. |
| 2006/0241385 A1 | 10/2006 | Dietz |
| 2006/0264935 A1 | 11/2006 | White |
| 2007/0088359 A1 | 4/2007 | Woods et al. |
| 2007/0093813 A1 | 4/2007 | Callahan, II et al. |
| 2007/0093832 A1 | 4/2007 | Abdelgany |
| 2007/0100341 A1 | 5/2007 | Reglos et al. |
| 2007/0161985 A1 | 7/2007 | Demakus et al. |
| 2007/0198014 A1 | 8/2007 | Graf et al. |
| 2007/0227216 A1 | 10/2007 | Schalliol |
| 2007/0288011 A1 | 12/2007 | Logan |
| 2007/0288030 A1 | 12/2007 | Metzger et al. |
| 2008/0086127 A1 | 4/2008 | Patterson et al. |
| 2008/0114370 A1 | 5/2008 | Shoenefeld |
| 2008/0161815 A1 | 7/2008 | Shoenefeld et al. |
| 2008/0183214 A1 | 7/2008 | Copp et al. |
| 2008/0255564 A1 | 10/2008 | Michelson |
| 2008/0257363 A1 | 10/2008 | Schoenefeld et al. |
| 2008/0275452 A1 | 11/2008 | Lang et al. |
| 2008/0306552 A1 | 12/2008 | Winslow |
| 2008/0312659 A1 | 12/2008 | Metzger et al. |
| 2008/0319491 A1 | 12/2008 | Schoenefeld |
| 2009/0076555 A1 | 3/2009 | Lowry et al. |
| 2009/0087276 A1 | 4/2009 | Rose |
| 2009/0088674 A1 | 4/2009 | Caillouette et al. |
| 2009/0088761 A1 | 4/2009 | Roose et al. |
| 2009/0088763 A1 | 4/2009 | Aram et al. |
| 2009/0093816 A1 | 4/2009 | Roose et al. |
| 2009/0099567 A1 | 4/2009 | Zajac |
| 2009/0105760 A1 | 4/2009 | Frey |
| 2009/0110498 A1 | 4/2009 | Park |
| 2009/0138020 A1 | 5/2009 | Park et al. |
| 2009/0187194 A1 | 7/2009 | Hamada |
| 2009/0198277 A1 | 8/2009 | Gordon et al. |
| 2009/0254093 A1 | 10/2009 | White et al. |
| 2009/0270868 A1 | 10/2009 | Park et al. |
| 2009/0326537 A1 | 12/2009 | Anderson |
| 2010/0016984 A1 | 1/2010 | Trabish |
| 2010/0049195 A1 | 2/2010 | Park et al. |
| 2010/0082035 A1 | 4/2010 | Keefer |
| 2010/0087829 A1 | 4/2010 | Metzger et al. |
| 2010/0100193 A1 | 4/2010 | White |
| 2010/0152782 A1 | 6/2010 | Stone et al. |
| 2010/0191244 A1 | 7/2010 | White et al. |
| 2010/0217270 A1 | 8/2010 | Polinski et al. |
| 2010/0217336 A1 | 8/2010 | Crawford et al. |
| 2010/0305700 A1 | 12/2010 | Ben-Arye et al. |
| 2010/0324692 A1 | 12/2010 | Uthgenannt et al. |
| 2011/0015636 A1 | 1/2011 | Katrana et al. |
| 2011/0015639 A1 | 1/2011 | Metzger et al. |
| 2011/0046735 A1 | 2/2011 | Metzger et al. |
| 2011/0054478 A1 | 3/2011 | Vanasse et al. |
| 2011/0071533 A1 | 3/2011 | Metzger et al. |
| 2011/0093023 A1 | 4/2011 | Lee et al. |
| 2011/0093086 A1 | 4/2011 | Witt et al. |
| 2011/0160736 A1 | 6/2011 | Meridew et al. |
| 2011/0160867 A1 | 6/2011 | Meridew et al. |
| 2011/0166578 A1 | 7/2011 | Stone et al. |
| 2011/0184419 A1 | 7/2011 | Meridew et al. |
| 2011/0184526 A1 | 7/2011 | White et al. |
| 2011/0190899 A1 | 8/2011 | Pierce et al. |
| 2011/0213376 A1 | 9/2011 | Maxson et al. |
| 2011/0218545 A1 | 9/2011 | Catanzarite et al. |
| 2011/0224674 A1 | 9/2011 | White et al. |
| 2011/0288433 A1 | 11/2011 | Kelleher et al. |
| 2012/0041445 A1 | 2/2012 | Roose et al. |
| 2012/0130434 A1 | 5/2012 | Stemniski et al. |
| 2012/0150243 A9 | 6/2012 | Crawford et al. |
| 2012/0179259 A1 | 7/2012 | McDonough et al. |
| 2012/0215315 A1 | 8/2012 | Hochschuler et al. |
| 2012/0245587 A1 | 9/2012 | Fang |
| 2013/0006251 A1 | 1/2013 | Aram et al. |
| 2013/0053854 A1 | 2/2013 | Schoenefeld et al. |
| 2013/0060278 A1* | 3/2013 | Bozung .............. A61B 17/1746 606/205 |
| 2013/0110174 A1 | 5/2013 | Marik |
| 2013/0123850 A1 | 5/2013 | Schoenefeld et al. |
| 2014/0137618 A1 | 5/2014 | Isaacs |
| 2014/0379032 A1 | 12/2014 | Hennard |
| 2015/0047410 A1 | 2/2015 | Petit et al. |
| 2015/0119939 A1 | 4/2015 | Frey et al. |
| 2015/0127053 A1 | 5/2015 | Maruenda Paulino et al. |
| 2015/0297249 A1 | 10/2015 | Catanzarite |

(56) References Cited

U.S. PATENT DOCUMENTS

| | | |
|---|---|---|
| 2016/0030067 A1 | 2/2016 | Frey et al. |
| 2016/0270802 A1 | 9/2016 | Fang et al. |
| 2017/0215857 A1 | 8/2017 | D'Urso |

FOREIGN PATENT DOCUMENTS

| | | |
|---|---|---|
| CN | 201275138 | 7/2009 |
| CN | 201404283 | 2/2010 |
| CN | 101390773 | 11/2010 |
| CN | 101953713 | 1/2011 |
| CN | 104306061 | 1/2015 |
| CN | 105078563 | 11/2015 |
| CN | 106175911 | 12/2016 |
| CN | 104224306 | 8/2017 |
| DE | 102013110699 | 4/2015 |
| DE | 202014011170 U1 | 4/2018 |
| EP | 2168507 | 3/2010 |
| EP | 2957244 | 12/2015 |
| EP | 2749235 | 8/2017 |
| EP | 3381382 | 10/2018 |
| FR | 3012030 | 12/2015 |
| FR | 3023655 | 4/2018 |
| GB | 2447702 | 9/2008 |
| JP | 10071157 | 3/1998 |
| JP | 2002531214 | 9/2002 |
| JP | 2005118569 | 5/2005 |
| JP | 2006528533 | 12/2006 |
| JP | 2007502692 | 2/2007 |
| JP | 2007510482 | 4/2007 |
| JP | 2012143379 | 8/2012 |
| WO | WO2004071314 | 8/2004 |
| WO | 200503710 | 4/2005 |
| WO | 2006039266 | 4/2006 |
| WO | 2006066053 | 6/2006 |
| WO | 2006079531 | 8/2006 |
| WO | 2007037920 | 4/2007 |
| WO | 2007145937 | 12/2007 |
| WO | 2008027549 | 3/2008 |
| WO | WO2009004625 | 1/2009 |
| WO | 2009035358 | 3/2009 |
| WO | WO2006017641 | 4/2009 |
| WO | WO2008157412 | 4/2009 |
| WO | 2009129063 | 10/2009 |
| WO | 2009105106 | 12/2009 |
| WO | WO2010033431 | 3/2010 |
| WO | 2010148103 | 12/2010 |
| WO | 2011041398 | 4/2011 |
| WO | 2011080260 | 7/2011 |
| WO | 2011106711 | 9/2011 |
| WO | 2011109260 | 9/2011 |
| WO | WO2012082164 | 6/2012 |
| WO | 2012152900 | 11/2012 |
| WO | 2013041618 | 3/2013 |
| WO | WO2013041618 | 3/2013 |
| WO | 2013104682 | 7/2013 |
| WO | WO2013169674 | 11/2013 |
| WO | WO2013173700 | 11/2013 |
| WO | WO2014070889 | 5/2014 |
| WO | 2014088801 | 6/2014 |
| WO | WO2014090908 | 6/2014 |
| WO | WO2014095853 | 6/2014 |
| WO | 2014143762 | 9/2014 |
| WO | WO2014198279 | 12/2014 |
| WO | WO2016148675 | 9/2016 |

OTHER PUBLICATIONS

Juvinall et al. "Fundamentals of Machine Component Design," Wiley, Dec. 2004, 4th edition, 5 pages [retrieved from: http://tocs.ulb.tu-darmstadt.de/178455539.pdf].

International Search Report and Written Opinion for International (PCT) Patent Application No. PCT/US08/08637 dated Oct. 20, 2009, 8 pages.

International Preliminary Report on Patentability for International (PCT) Patent Application No. PCT/US08/08637 dated Jan. 19, 2010, 6 pages.

Official Office Action for Australian Patent Application No. 52008276577 dated Nov. 2, 2012 5 pages.

Notice of Acceptance for Australia Patent Application No. 2008276577, dated Jan. 21, 2014 2 pages.

Official Action for Australia Patent Application No. 2014202363, dated Nov. 14, 2014 6 pages.

Official Action for Australia Patent Application No. 2014202363, dated Apr. 1, 2015 3 pages.

Official Action for Australia Patent Application No. 2014202363, dated Aug. 3, 2015 4 pages.

Official Action for Australia Patent Application No. 2014202363, dated Sep. 18, 2015 6 pages.

Official Action for Canada Patent Application No. 2,693,682, dated Jan. 21, 2014 2 pages.

Extended European Search Report for European Patent Application No. 08794499.7 dated Oct. 8, 2012, 13 pages.

Official Action for European Patent Application No. 08794499.7, dated Jul. 2, 2013 6 pages.

Notice of Allowance for European Patent Application No. 08794499.7 dated Mar. 19, 2014 6 pages.

Extended Search Report for European Patent Application No. 14180580.4, dated Oct. 15, 2015 9 pages.

Official Action (with English Translation) for Japanese Patent Application No. 2010-517004 dated Jan. 15, 2013 6 pages.

Official Action (with English Translation) for Japanese Patent Applicaiton No. 2010-517004 dated Oct. 11, 2013 4 pages.

Re-Examination Report with English Translation for Japan Patent Application No. 2010-517004, dated Apr. 1, 2014 2 pages.

Official Action with English Translation for Japan Patent Application No. 2010-517004, dated Dec. 5, 2014 4 pages.

Official Action for U.S. Appl. No. 12/172,996, dated Apr. 13, 2011 5 pages Restriction Requirement.

Official Action for U.S. Appl. No. 12/172,996, dated Jun. 9, 2011 10 pages.

Official Action for U.S. Appl. No. 12/172,996, dated Dec. 7, 2011 10 pages.

Official Action for U.S. Appl. No. 12/172,996, dated Sep. 25, 2014 11 pages.

Official Action for U.S. Appl. No. 12/172,996, dated May 21, 2015 11 pages.

Official Action for U.S. Appl. No. 14/478,744, dated Jul. 30, 3015 8 pages.

"Introducing IntelliSense Drill Technology®", McGinley Orthopaedic Innovations, 1 page, [captured Feb. 29, 2016 from: http://web.archive.org/web/20160229042028/http://www.mcginleyorthopaedicinnovations.come/index/php?/drill].

Brussel et al. "Medical Image-Based Design of an Individualized Surgical Guide for Pedicle Screw Insertion." 18th Annual International Conference of the IEEE Engineering in Medicine and Biology Society, Amsterdam 1996, pp. 225-226.

Dai et al. "Surgical treatment of the Osteoporotic spine with bone cement-injectable cannulated pedicle screw fixation: technical description and preliminary application in 43 patients, " Clinics, Feb. 2015, vol. 70, No. 2, pp. 114-119.

Hong et al. "Binder jetting 3D printing and alloy development of new biodegradable Fe—Mn—Ca/Mg alloys," Acta Biomaterialia, Nov. 2016, vol. 45, pp. 375-386 (Abstract Only) 4 pages.

Jakus et al. "Hyperelastic "bone": A highly versatile, growth factor-free, osteoregenerative, scalable, and surgically friendly biomaterial," Science Translational Medicine, Sep. 2016, vol. 8, No. 358, pp. 358ra127 (Abstract only) 5 pages.

Lu et al. "A novel computer-assisted drill guide template for lumbar pedicle screw placement: a cadaveric and clinical study." The International Journal of Medical Robotics and Computer Assisted Surgery, Jun. 2009, Voi. 5, No. 2, pp. 184-191. (Abstract only).

Lu et al. "A Noverl Patient-Specific Navigational Template for Cervical Pedicle Screw Placement," Spine, Dec. 15, 2009, vol. 34, No. 26, pp. E959-E966 (Abstract only).

(56) References Cited

OTHER PUBLICATIONS

Owen et al. "Rapid prototype patient-specific drill template for cervical pedicle screw placement." Computer Aided Surgery, Sep. 2007, vol. 12, No. 5, pp. 303-308 (Abstract Only).
Ryken et al. "Image-based drill templates for cervical pedicle screw placement Laboratory investigation," Journal of Neurosurgery, Jan. 2009, vol. 10, No. 1 (Abstract Only).
Yin et al. "Computer aid designed digital targeting template of pedicle of vertebral arch for atlantoaxial nailing," IT in Medicine & Education, 2009. ITIME '09. Aug. 14-16, 2009, vol. 1 (Abstract Only).
ntemational Search Report and Written Opinion for International (PCT) Patent Application No. PCT/US11/42412 dated Nov. 8, 2011, 8 pages.
International Preliminary Report on Patentability for international (PCT) Patent Application No. PCT/US11/42412 dated Jan. 17, 2013, 7 pages.
Official Action for Australian Patent Application No. 2011276468 dated Apr. 10, 2013 3 pages.
Official Action for Canada Patent Application No. 2,802,094, dated Feb. 14, 2017, 4 pages.
Partial Search Report for European Patent Application No. 11804191.2, dated Jan. 20, 2015, 6 pages.
Extended Search Report for European Patent Application No. 11804191.2 dated May 7, 2015 8 pages.
Official Action for European Patent Application No. 11804191.2, dated Feb. 17, 2017 5 pages.
Official Action with English Translation for Japan Patent Application No. 2013-518663, dated May 12, 2015 4 pages.
Notice of Allowance with English Translation for Japan Patent Application No. 2013-518663 dated Dec. 8, 2015 4 pages.
International Search Report and Written Opinion for International (PCT) Patent Application No. PCT/US2013/036535, dated Jun. 26, 2013, 8 pages.
International Preliminary Report on Patentability for International (PCT) Patent Application No. PCT/US2013/036535, dated Oct. 30, 2014, 7 pages.
Official Action with English Translation for China Patent Application No. 201380030638.3, dated May 25, 2016 11 pages.
Official Action with English Translation for China Patent Application No. 201380030638.3, dated Feb. 4, 2017 6 pages.
Extended Search Report for European Patent Application No. 13778164.7, dated Feb. 17, 2016 10 pages.
Notice of Allowance with English Translation for Japan Patent Application No. 2015-507078, dated Jan. 10, 2017 4 pages.
Official Action with English Translation for Russia Patent Application No. 2014143528/14, dated Jan. 13, 2017 8 pages.
International Search Report and Written Opinion for International (PCT) Patent Application No. PCT/US15/32356, dated Oct. 28, 2015 10 pages.
International Preliminary Report on Patentability for International (PCT) Patent Application No. PCT/US2015/032356, dated Dec. 15, 2016 7 pages.
International Search Report and Written Opinion for International (PCT) Patent Application No. PCT/US2016/056970, dated 10, 2017 13 pages.
International Search Report and Written Opinion for International (PCT) Patent Application No. PCT/US2014/041379, dated Oct. 28, 2014, 7 pages.
International Preliminary Report on Patentability for International (PCT) Patent Application No. PCT/US2014/041379, dated Dec. 17, 2015 6 pages.
Official Action for Canada Patent Application No. 2,914,005, dated Feb. 3, 2017 3 pages.
Official Action for U.S. Appl. No. 13/172,683, dated Sep. 10, 2013 7 pages.
Office Action for U.S. Appl. No. 13/172,683, dated Feb. 24, 2014 10 pages.
Notice of Allowance for U.S. Appl. No. 13/172,683, dated Apr. 23, 2014 7 pages.
Notice of Allowance for U.S. Appl. No. 29/409,734, dated May 11, 2012 8 pages.
Notice of Allowance for U.S. Appl. No. 29/427,918, dated Oct. 15, 2012 9 pages.
Notice of Allowance for U.S. Appl. No. 19/432,668 dated Nov. 27, 2013 11 pages.
Notice of Allowance for U.S. Appl. No. 29/476,709, dated Nov. 6, 2015, 8 pages.
Notice of Allowance for U.S. Appl. No. 29/476,705, dated Oct. 7, 2015, 8 Pages.
Notice of Allowance for U.S. Appl. No. 29/476,699, dated Oct. 2, 2015, 8 pages.
Notice of Allowance for U.S. Appl. No. 29/496,231, dated Jul. 23, 2015 10 pages.
Notice of Allowance for U.S. Appl. No. 29/538,633, dated Jan. 6, 2016 10 pages.
Official Action for U.S. Appl. No. 13/841,069, dated Jul. 31, 2014 9 pages.
Notice of Allowance for U.S. Appl. No. 13/841,069, dated Sep. 18, 2014 7 pages.
Office Action for U.S. Appl. No. 14/298,634, dated Apr. 27, 2015, 8 pages.
Office Action for U.S. Appl. No. 14/298,634, dated Jul. 7, 2015 6 pages.
Notice of Allowance for U.S. Appl. No. 14/298,624, dated Oct. 7, 2015 7 pages.
Notice of Allowance for U.S. Appl. No. 14/883,299, dated Mar. 20, 2017 12 pages.

* cited by examiner

DRILL APPARATUS AND SURGICAL FIXATION DEVICES AND METHODS FOR USING THE SAME

CROSS-REFERENCE TO RELATED APPLICATIONS

This application is a continuation-in-part of U.S. patent application Ser. No. 15/416,975, filed on Jan. 26, 2017. This application claims priority under 35 U.S.C. § 119(e) to U.S. Provisional Application No. 62/373,855, filed Aug. 11, 2016.

FIELD OF THE INVENTION

The present disclosure relates to the field of medical devices generally. More specifically, the present disclosure relates to a drill apparatus configurable for use with a variety of customized or standardized devices, for example, implants and guides for use in a surgical setting. Systems and methods for using the foregoing apparatus and devices also disclosed herein.

BACKGROUND OF THE INVENTION

Many prior art devices used to achieve various drilling tasks or related activities suffer from significant disadvantages, such as poor stability and/or accuracy, difficulty in handling and operating in confined spaces, poor visibility and other disadvantages. For example, many drilling apparatus have fast moving parts, rotating parts and/or vibrating parts which prevent the drilling apparatus to be secured in a comfortable and fixed position while in use or which significantly impair the visibility and operation of the operable end of the apparatus. Furthermore, several prior art drilling apparatus have little or no depth control or accuracy measures with respect to over-drilling or under-drilling, as the application may tend to require. These problems and shortcomings are even more noticeable when considering prior art drills for use in surgical settings or which otherwise require precision.

In addition to the shortcomings with drilling apparatus, fixation devices can also suffer from various shortcomings. For example, pedicle screws are subject to relatively high failure rates, which is often attributed to a failure of the bone-screw interface. Screws for use in surgical settings may also be limited for use in only certain boney anatomies, or with only certain types of drilling apparatus.

Accordingly, there is a need for an improved drilling apparatus that decreases drilling times, enhances depth control, as well as stability and accuracy when performing drilling operations, and which otherwise overcomes the disadvantages of the prior art. In particular, there is a need for a drill apparatus that does not require the user to move the drill body during the drilling operation. There is also a strong need for a drilling device that improves patient safety, in part by reducing the risk of anterior breaches during certain surgical procedures requiring the use of drilling apparatus.

The prior art also fails to teach a system for creating a suite of surgical apparatus based on the data set derived from a patient's MRI or CT scan. For example, the availability of patient-specific data (for example, a vertebral body) may allow a surgeon to accommodate for subtle variations in the position and orientation of a plate, screw, or other bone anchor to avoid particular boney anatomy, or irregularities in the positioning and alignment of the adjoining vertebral bodies. As another example, the use of patient data may also assist a surgeon in selecting a desired trajectory for an implantable device so as to avoid, for example, crossing the pedicle wall and violating the spinal canal during a spine-related procedure. The use of patient-specific data permits the surgeon to avoid these types of mistakes by creating and utilizing customized tools and instruments, which may comprise specific orientation, end-stops/hard stops, or other safety related features to avoid over-torque or over-insertion of an associated device. This data also permits the surgeon to create a patient-contacting surface that is oriented to match one or more of the anatomical features derived from the data set, and thereby quickly and efficiently locate and place devices with corresponding patient-contacting surface(s) in the appropriate location and orientation.

It would therefore be advantageous to provide apparatus suitable for use with a surgical procedure that is adapted and/or configured and/or capable of conforming to a plurality of anatomical features of a particular patient, and/or to one or more additional apparatus to assist the surgeon in completing the surgical procedure(s) safely and efficiently, and that otherwise significantly reduces, if not eliminates, the problems and risks noted above. Other advantages over the prior art will become known upon review of the Summary and Detailed Description and the appended claims.

BRIEF SUMMARY OF THE INVENTION

Embodiments of the present disclosure provide systems, methods, and devices for performing drilling operations, including but not limited to in a surgical setting. The embodiments disclosed herein further relate to guides for use with the drilling apparatus described in various embodiments, as well as for use with other apparatus.

One aspect of the present disclosure relates to a drill apparatus, which may be held in a user's hand(s). The drill preferably comprises a housing or body, a drill bit, which preferably extends out from the drill body, and which may be based on a pre-programmed depth. In embodiments, the drill bit is adjustable relative to the body of the drill, and may comprise a dynamic telescoping mechanism for enhancing the position of the drill bit, and thereby the depth of the associated drilling operation to be performed by the user.

Pre-programmed depths for determining the drill bit extension from the body of the drill may be determined, for example, by using CAD software, 3-dimensional models, or in certain embodiments from CT scans or xrays of a particular patient. The drill apparatus preferably comprises an internal motor, with one or more computational apparatus to establish and control the rotation and direction of the drill bit, the drill bit depth, etc.

The user may program the drill depth into the drill using a computer or graphic or other interface preferably located on the body of the drill. In embodiments, a flash-drive or memory card can also be loaded with information and accepted by (i.e., downloaded to) computational machinery housed within the drill. Pre-determined depths may also be read by the drill using markings or indicia located on, for example, a drilling guide, an RFID marker, or a barcode, including one of the foregoing placed on a fixation device to be used with the drill apparatus. In this embodiment, the drill apparatus preferably comprises at least one sensor or scanner that is configured to read or sense the required depth based on the indicia, then drill to the associated depth correlating to that indicia.

In another embodiment, the drill bit may extend from the drill body and/or automatically "zero" its depth in relation to the surface to be drilled. The user may then initiate a drilling operation, and the drill will begin rotating and advance the drill bit to the pre-determined depth from this "zero" depth position. After the drill bit reaches the pre-determined depth, the drill will stop and not proceed further, thereby preventing over travel. After the maximum drill depth has been reached, and the user switches the drill apparatus from a drilling operation to an idle state, the drill bit may automatically retract back into the drill body, thereby preventing injury or contamination.

Incorporated by reference in their entireties are the following U.S. patents and patent applications directed generally to methods and apparatus related to surgical procedures, thus providing written description support for various aspects of the present disclosure. The U.S. patents and pending applications incorporated by reference are as follows: U.S. Pat. Nos. 7,957,824, 7,844,356, 7,658,610, 6,830,570, 6,368,325, 3,486,505 and U.S. Pat. Pub. Nos. 2010/0217336, 2009/0138020, 2009/0087276, 2008/0161817, 2008/0114370, and 2007/0270875.

Additionally, U.S. Pat. Nos. 8,758,357, 8,870,889, 9,198,678 and 9,642,633 are incorporated by reference for the express purpose of illustrating systems and methods for creating a surgical or cutting guide, such as the ones described herein, using additive manufacturing or other techniques, wherein the device incorporates one or more patient-matched surfaces or is otherwise customized to a particular patient.

The phrases "at least one," "one or more," and "and/or," as used herein, are open-ended expressions that are both conjunctive and disjunctive in operation. For example, each of the expressions "at least one of A, B and C," "at least one of A, B, or C," "one or more of A, B, and C," "one or more of A, B, or C," and "A, B, and/or C" means A alone, B alone, C alone, A and B together, A and C together, B and C together, or A, B and C together.

Unless otherwise indicated, all numbers expressing quantities, dimensions, conditions, and so forth used in the specification and claims are to be understood as being approximations which may be modified in all instances as required for a particular application of the novel apparatus described herein.

The term "a" or "an" entity, as used herein, refers to one or more of that entity. As such, the terms "a" (or "an"), "one or more" and "at least one" can be used interchangeably herein.

The use of "including," "comprising," or "having" and variations thereof herein is meant to encompass the items listed thereafter and equivalents thereof as well as additional items. Accordingly, the terms "including," "comprising," or "having" and variations thereof can be used interchangeably herein.

It shall be understood that the term "means" as used herein shall be given its broadest possible interpretation in accordance with 35 U.S.C., Section 112(f). Accordingly, a claim incorporating the term "means" shall cover all structures, materials, or acts set forth herein, and all of the equivalents thereof. Further, the structures, materials, or acts and the equivalents thereof shall include all those described in the Summary, Brief Description of the Drawings, Detailed Description, Abstract, and Claims themselves.

The Summary is neither intended, nor should it be construed, as being representative of the full extent and scope of the present disclosure. Moreover, references made herein to "the present disclosure" or aspects thereof should be understood to mean certain embodiments of the present disclosure, and should not necessarily be construed as limiting all embodiments to a particular description. The present disclosure is set forth in various levels of detail in the Summary as well as in the attached drawings and the Detailed Description, and no limitation as to the scope of the present disclosure is intended by either the inclusion or non-inclusion of elements or components when describing certain embodiments herein. Additional aspects of the present disclosure will become more readily apparent from the Detailed Description, particularly when taken together with the drawings.

The above-described benefits, embodiments, and/or characterizations are not necessarily complete or exhaustive, and in particular, as to the patentable subject matter disclosed herein. Other benefits, embodiments, and/or characterizations of the present disclosure are possible utilizing, alone or in combination, as set forth above and/or described in the accompanying figures and/or in the description herein below.

BRIEF DESCRIPTION OF THE DRAWINGS

The accompanying drawings, which are incorporated herein and constitute a part of the specification, illustrate embodiments of the disclosure, and together with the Summary and the Detailed Description serve to explain the principles of these embodiments. In certain instances, details that are not necessary for an understanding of the disclosure or that render other details difficult to perceive may have been omitted. It should be understood, of course, that the present disclosure is not necessarily limited to the particular embodiments illustrated herein. Additionally, it should be understood that the drawings are not necessarily to scale. In the drawings.

Figure 1:
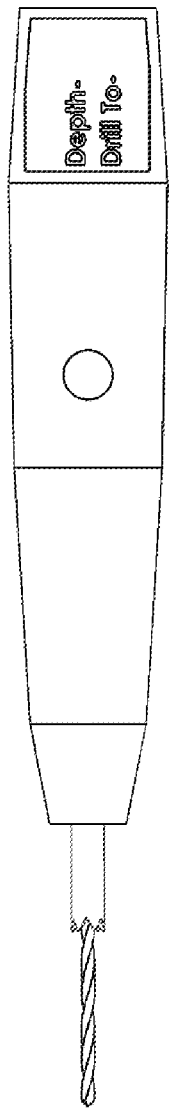
FIG. 1 shows the drilling apparatus according to one embodiment of the present disclosure where the bit is in an extended position.

Similar components and/or features may have the same reference number. Components of the same type may be distinguished by a letter following the reference number. If only the reference number is used, the description is applicable to any one of the similar components having the same reference number.

DETAILED DESCRIPTION OF THE INVENTION

The present disclosure has significant benefits across a broad spectrum of endeavors. It is the Applicant's intent that this specification and the claims appended hereto be accorded a breadth in keeping with the scope and spirit of the disclosure and various embodiments disclosed, despite what might appear to be limiting language imposed by specific examples disclosed in the specifications. To acquaint persons skilled in the pertinent arts most closely related to the present disclosure, preferred and/or exemplary embodiments are described in detail without attempting to describe all of the various forms and modifications in which the novel apparatus, devices, systems and methods might be embodied. As such, the embodiments described herein are illustrative, and as will become apparent to those skilled in the arts, may be modified in numerous ways within the spirit of the disclosure.

By way of providing additional background, context, and to further satisfy the written description requirements of 35 U.S.C. § 112, the following are incorporated by reference in their entireties for the express purpose of explaining and further describing the various tools and other apparatus commonly associated therewith surgical procedures, including minimally invasive surgery ("MIS") procedures: U.S. Pat. No. 6,309,395 to Smith et al.; U.S. Pat. No. 6,142,998 to Smith et al.; U.S. Pat. No. 7,014,640 to Kemppanien et al.; U.S. Pat. No. 7,406,775 to Funk, et al.; U.S. Pat. No. 7,387,643 to Michelson; U.S. Pat. No. 7,341,590 to Ferree; U.S. Pat. No. 7,288,093 to Michelson; U.S. Pat. No. 7,207,992 to Ritland; U.S. Pat. No. 7,077,864 Byrd III, et al.; U.S. Pat. No. 7,025,769 to Ferree; U.S. Pat. No. 6,719,795 to Cornwall, et al.; U.S. Pat. No. 6,364,880 to Michelson; U.S. Pat. No. 6,328,738 to Suddaby; U.S. Pat. No. 6,290,724 to Marino; U.S. Pat. No. 6,113,602 to Sand; U.S. Pat. No. 6,030,401 to Marino; U.S. Pat. No. 5,865,846 to Bryan, et al.; U.S. Pat. No. 5,569,246 to Ojima, et al.; U.S. Pat. No. 5,527,312 to Ray; and U.S. Pat. Appl. No. 2008/0255564 to Michelson.

Several advantages of an improved drill apparatus have previously been described herein, but for convenience, the following advantages are achieved by the drill apparatus contemplated by this disclosure: the drill apparatus may be handheld, and in one embodiment may be battery powered to eliminate the need for cords or cables; the drill apparatus may comprise a drill bit selectively housed in the drill body, which avoids injury to the user and contamination to those who come into contact with the drill bit; The drill apparatus may comprise a modular design allowing for changing out different sized drill bits or reamers; the drill apparatus may comprise a sleeve located proximate to the tip of drill for mating the drill with or guiding the drill bit through, for example, a cannula or surgical guide, as described in greater detail below.

The drill apparatus may additionally comprise or alternatively communicate with at least one sensor or scanner that is configured to read or sense the required depth based on one or more indicia, then drill to the associated depth correlating to the one or more indicia. The drill apparatus may comprise computational machinery to provide a user with the ability to program certain operations, safety features, etc., and which may further comprise the ability to read and/or write to a removable memory card. These and other advantages will be appreciated after reviewing the complete disclosure relating to various embodiments of the drilling apparatus described herein.

Several views of the drill apparatus described herein are shown in FIGS. 1-26. The drilling apparatus preferably comprises at least one user interface, which may display depth, speed, resistance or other measurements (for estimating bone quality). A user may quickly and easily adjust parameters of the drill apparatus via the interface, which may be comprised of a touch screen or other inputs, such as pushbuttons.

An integral display, may be provided, which preferably shows the precise depth of the drill bit and other settings, such as the level the drill is set for. A user may adjust these settings and/or preset levels in case there is a change in the pre-determined drill depth, or if the user decides to abort the current operation and implement a new plan.

Figure 2:
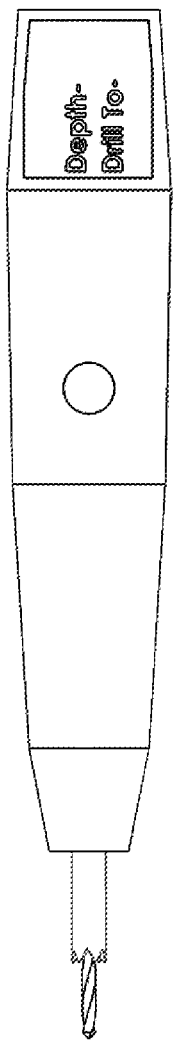
FIG. 2 shows the drilling apparatus of FIG. 1 where the bit is in a partially extended position.
Figure 3:
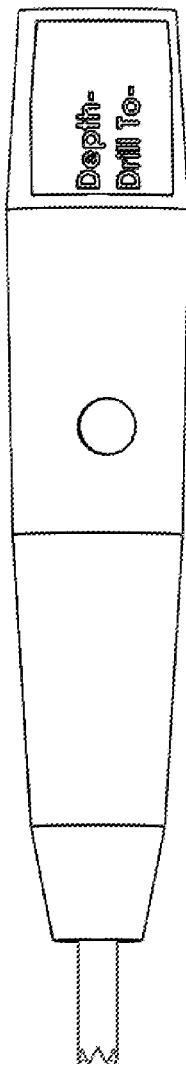
FIG. 3 shows the drilling apparatus of FIG. 1 where the bit is in a retracted position.

The programmable depth of the drilling apparatus is best illustrated in FIGS. 1-4. Referring now to FIG. 1, the drill apparatus is shown with the drill bit in a fully extended position. The display is depicted at the opposite end of the drill bit, but in alternate embodiments may be located centrally on the drill body or at the drill bit end of the drill apparatus. This display may indicate various parameters or other information of importance to the user, such as "Depth" and the "Drill To" quantities discussed elsewhere in this application. In FIG. 2, the drill apparatus of FIG. 1 is shown with the drill bit in a half-extended position. In FIG. 3, the drill bit is fully retracted. Variations on these positions are considered within the scope of the present disclosure. It is expressly understood that these drawings are not to scale, and in certain embodiments the drill bit may extend more or less than shown in the drawing figures.

Figure 4:
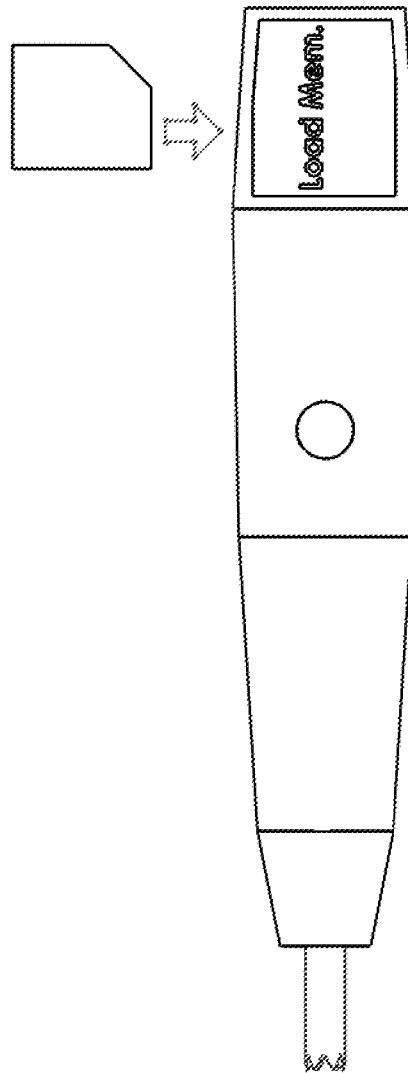
FIG. 4 shows the drilling apparatus of FIG. 1 with an integrated display and means for loading a program into the memory of the apparatus.

Referring now to FIG. 4, the drilling apparatus may comprise pre-programmed settings for each level in a human spine or other area of unique patient anatomy. Pre-surgical plans or pre-programmed depths for determining the drill bit extension from the body of the drill may be determined, for example, by using CAD software, 3-dimensional models, or in certain embodiments from CT scans or xrays of a particular patient. The drill apparatus preferably comprises an internal motor, with one or more computational apparatus to establish and control the rotation and direction of the drill bit, the drill bit depth, etc.

The user may initially program or customize the drill depth into the drill using a computer or graphic or other interface, preferably located on the body of the drill. A flash-drive or memory card can also be used, such as a card or drive loaded with information and ultimately accepted by (i.e., downloaded to) the computational machinery housed within the drill. Pre-determined depths may also be read by the drill using markings or indicia located on, for example, a drilling guide, an RFID marker, or a barcode, including such indicia located on a fixation device to be used with the drill apparatus.

The drill bit may extend from the drill body, and may automatically "zero" its depth in relation to the surface to be drilled. The user may then press a button switch or icon on the interface, and advance the drill bit to the pre-determined depth. After the drill bit reaches a pre-determined depth, the drill may be configured to stop and not proceed further, thereby preventing overtravel. The drill may further comprise a setting that achieves an "auto zero" when the drill bit contacts a certain resistance or hardness of material, for example, cortical bone. The drill may further comprise an automatic shut off or emergency stop sequence if secondary material density is contacted by the drill bit, such as in the event the bone face of a patient is pierced. These features may be used to prevent a surgeon from going through the vertebral body in a patient's spine, or other bones where a drilling procedure is required.

In other embodiments, the drill apparatus may be selectively programmed depending on the patient's bone quality, so that the drill may automatically detect how hard the materials are that the drill is to come into contact with (i.e., cortical vs cancellous bone), and therefore what speed, depth, power and acceleration is required to complete the drilling procedure. This information may be gathered from the CT scan or xray of the patient, and may either be programed into the drill (by using the graphic interface, for example) or may be downloaded to use with, by way of example, the drill.

The drill apparatus may also comprise an automatic shut off or "override" for various in/out/in trajectories. To further illustrate, the drill may automatically shut off if certain trajectories (such as those pre-determined by the user and loaded in the computational machinery of the drill) are departed from while the drill apparatus is in use. If the drill feels resistance, for instance the drill may manually or automatically mark the depth so the user may know where certain anatomical features, landmarks or impediments are located. In addition, a display associated with the drill apparatus may provide the drill depth and bone resistance or other critical information as the drill apparatus is in use.

Referring again to FIG. 4, the drill apparatus may accept one or more types of external devices, such as external drivers or memory cards, for downloading information to be accessed and/or used by computational machinery located within the drill body. In other embodiments, information and program may be received by the drill apparatus by the way of wireless or Bluetooth communication protocols, or otherwise without requiring a driver or card. Here, the display indicates that the user is to "Load Mem." or "memory" for programming the drill or achieving other functionality described herein.

Figure 5:
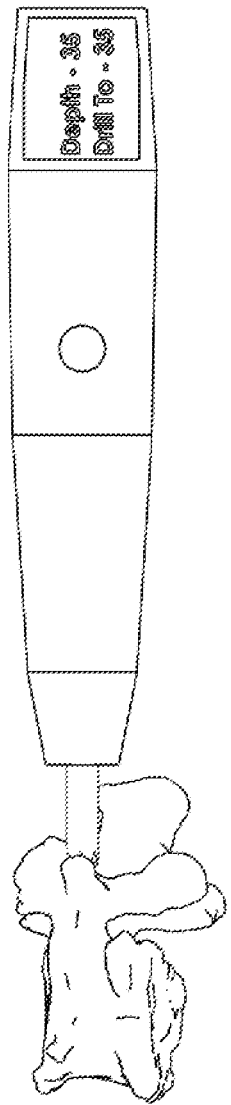
FIG. 5 shows the drilling apparatus of FIG. 1 aligned with a vertebral body and configured to drill to a desired depth.
Figure 6:
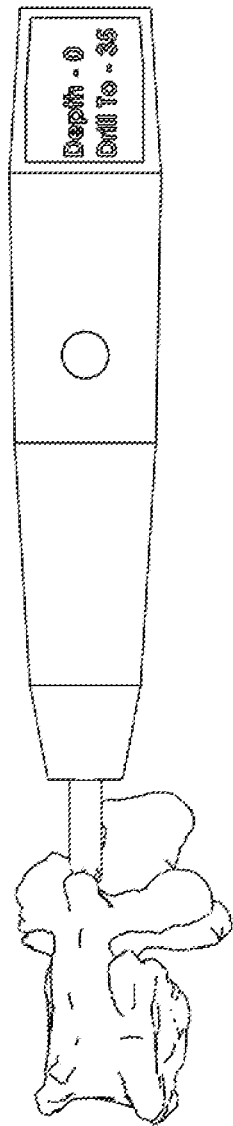
FIG. 6 shows the drilling apparatus of FIG. 5 where the display indicates the drill bit has extended into the vertebral body to the desired depth.

Referring now to FIGS. 5-6, the drill apparatus is shown relative to a patient's anatomical structure, as an example of the material to be used in conjunction with the drill apparatus described herein. As shown in these Figures, the drill apparatus may comprise a hard stop to prevent penetration of the drill apparatus into the anatomical feature beyond the extension of the drill bit from the drill body, which is programmable and may be pre-determined before the drill apparatus is to be used. The display may include a dynamic setting that changes as the drill bit extends from the drill body, as shown in FIGS. 5-6. In at least one embodiment, the drill apparatus may automatically dispense gel or foam to minimize bleeding in the patient or otherwise facilitate the drilling procedure. Reservoirs for housing the gel or foam may be either internal or external to the drill body.

The drill apparatus described herein may be used in conjunction with guides such as those commercially known as FIREFLY navigation guides, which are disclosed in part by U.S. Pat. Nos. 8,758,357, 8,870,889, 9,198,678 and 9,642,633. In this scenario, the drill apparatus would be centered over one of the cannula of the FIREFLY guides. The drill may then either be preset to drill the levels in order, or alternatively the drill could read/scan which level it is situated at using one of the indicia identified above (including RFID or "keyed" cannula or other devices bearing the indicia). Once the drill is placed above a guide cannula, the "instrument sleeve" contained within the drill advances into the guide to prevent the drill from contacting the guide. The drill is then advanced, per the procedure described above, and comes to a stop at a pre-determined depth associated with the particular guide or the imported patient data, or both. When used with FIREFLY guides described above, the drill may light up different colors to match the trajectories of the patient specific surgical plan on the display of the drill, such that the current level to be drilled would be displayed on the screen at any given time in the procedure or surgical plan.

Figure 7:
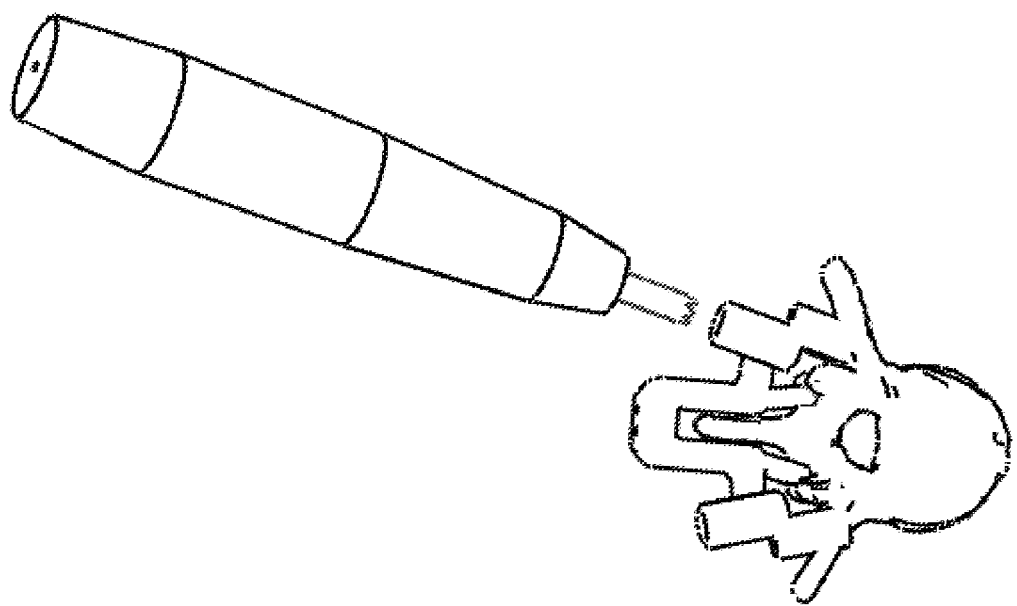
FIG. 7 shows the drilling apparatus according to another embodiment wherein the apparatus may be received within or otherwise used in connection with a surgical guide.
Figure 8:
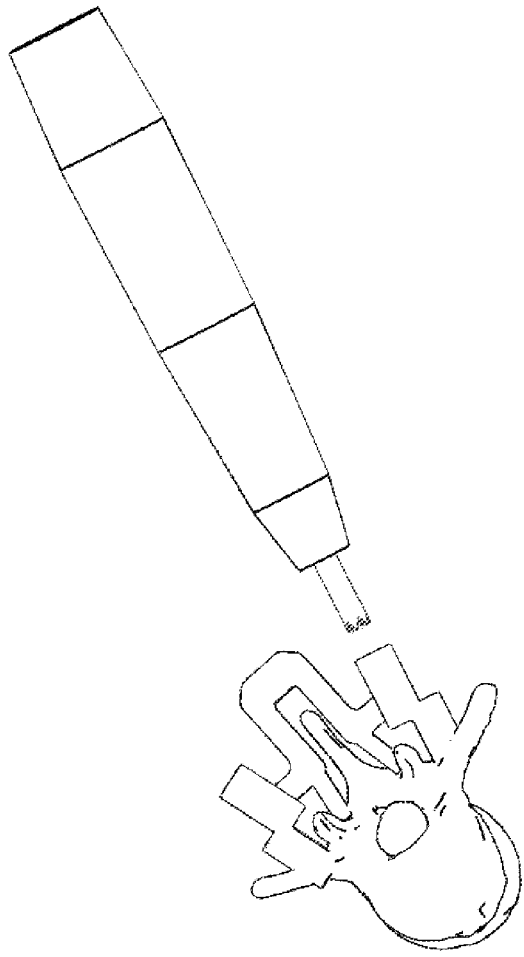
FIG. 8 shows another perspective view of the drilling apparatus of FIG. 7.

Referring now to FIG. 7, the drilling apparatus according to one embodiment may be received within or otherwise used in connection with a surgical guide, such as a FIREFLY navigation guide described above. According to this embodiment, the bit of the drilling apparatus is configured to be received within a hollow sleeve associated with the surgical guide such that the bit may only contact the boney anatomy in a certain location, and in a specific orientation, and in certain embodiments only to a certain depth. Further details are described in U.S. Pat. No. 9,642,633 which is incorporated herein by reference. FIG. 8 shows another perspective view of the embodiment shown in FIG. 7.

Figure 9:
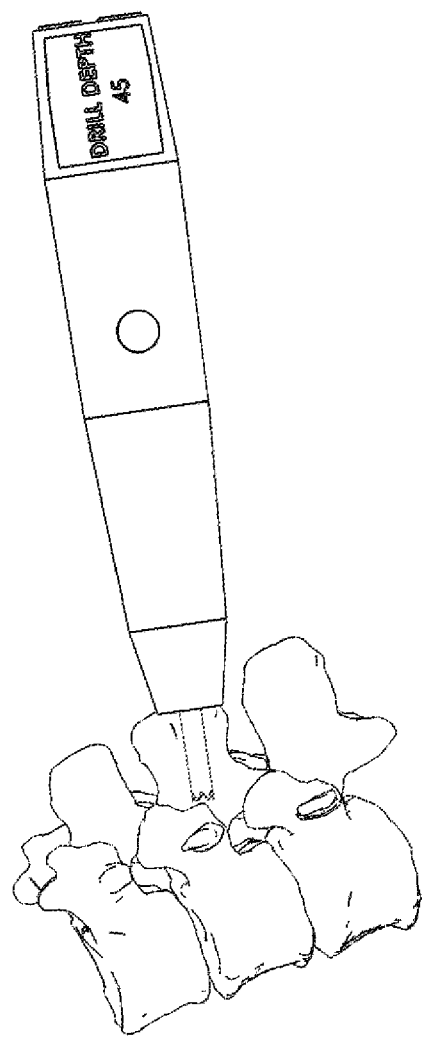
FIG. 9 shows a drilling apparatus according to another embodiment wherein the apparatus is aligned with a different vertebral body.

FIG. 9 shows a drilling apparatus according to another embodiment wherein the apparatus is aligned with a different vertebral body. In this embodiment, the drilling apparatus may be configured, either through programming or other means described herein, to extend from the chuck of the drill only by a certain amount, thereby providing accurate depth control. The programmed or configured depth may be reflected on the display of the apparatus, as shown in FIG. 9. Thus, even without a surgical guide and hard stops to prevent over-drilling, the drilling apparatus may be used in a manner to prevent drilling operation beyond a certain depth.

Figure 10:
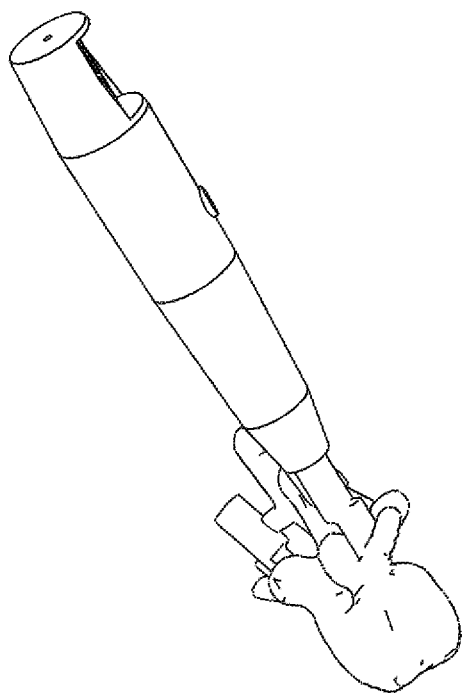
FIG. 10 shows the drilling apparatus according to another embodiment wherein the apparatus is received by a surgical guide.

FIG. 10 shows the drilling apparatus according to another embodiment wherein the apparatus is received by a surgical guide. According to this embodiment, the chuck of the drill may be received within the hollow sleeve of the surgical guide, providing stability and positional accuracy prior to operating the drill. In this manner, the drilling apparatus may be pre-programmed with a controlled depth, assuming that the chuck of the drill is going to be positioned in the hollow sleeve. Once the drill is in position relative to the guide, the bit may extend from the chuck and into the boney anatomy to the pre-programmed depth. Once completed, the operation may also include a program to retract the bit into the chuck before the drill is removed from the surgical guide.

Figure 11:
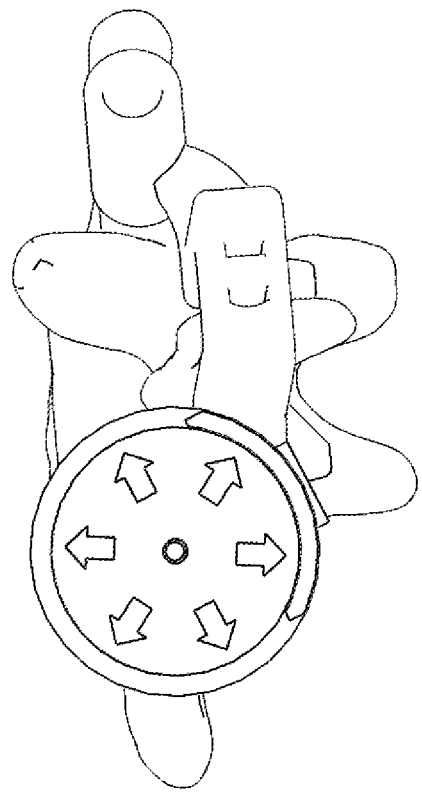
FIG. 11 shows a rear elevation view of the drilling apparatus shown in FIG. 10.
Figure 12:
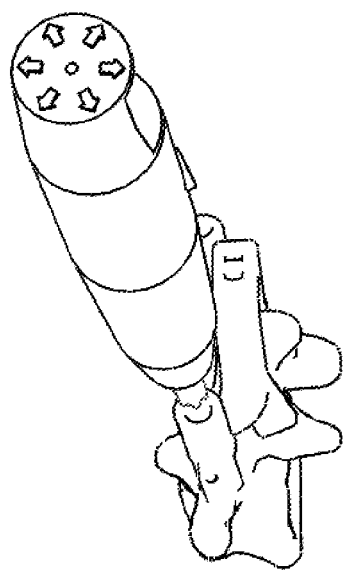
FIGS. 12-15 show alternate views of the drilling apparatus depicted in FIG. 10.
Figure 13:
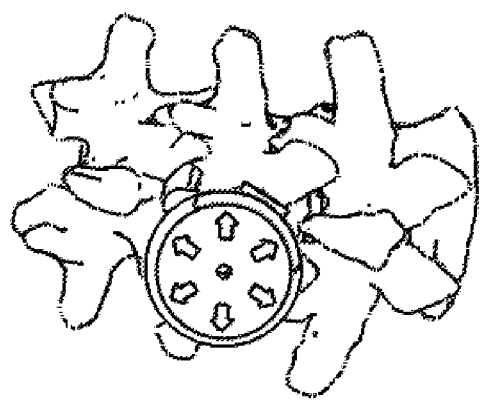
Figure 14:
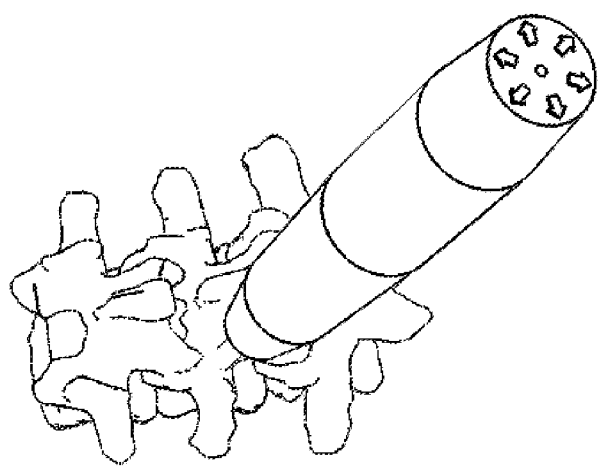
Figure 15:
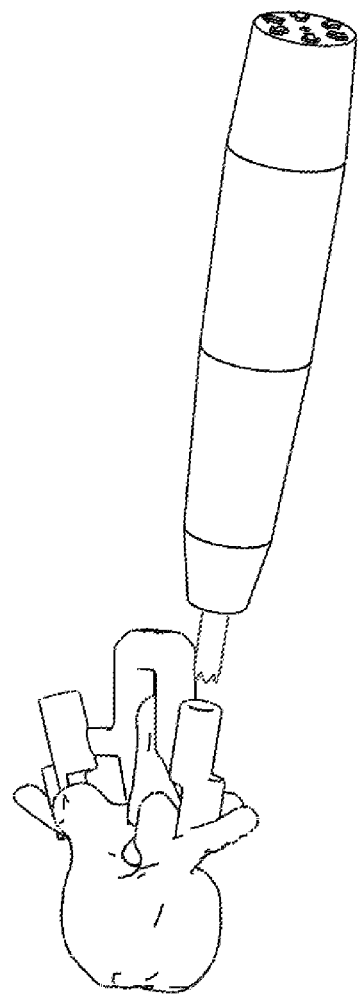

FIG. 11 shows a rear elevation view of the drilling apparatus shown in FIG. 10. In this embodiment, one or more indicia on the body of the drill may provide signals to the operator and provide instruction on which direction to move the proximal end of the drilling apparatus to achieve the appropriate alignment and orientation. For example, one of the arrows shown in FIG. 11 may illuminate, either temporarily or permanently, to indicate the proximal end of the drilling apparatus needs to move in the direction of the arrow to achieve the desired trajectory of the drill bit. While this embodiment is shown with the surgical guide of FIG. 10, it is expressly understood that these features may be incorporated with any of the embodiments described herein. For further illustration of this embodiment, FIGS. 12-15 are provided and depict alternate views of the drilling apparatus depicted in FIG. 10.

Figure 16:
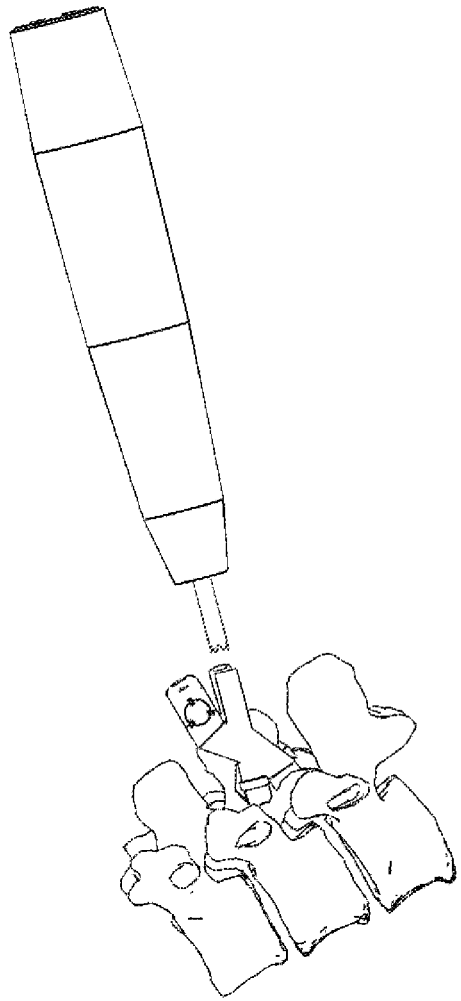
FIG. 16 shows a drilling apparatus according to another embodiment aligned with a different surgical guide.
Figure 17:
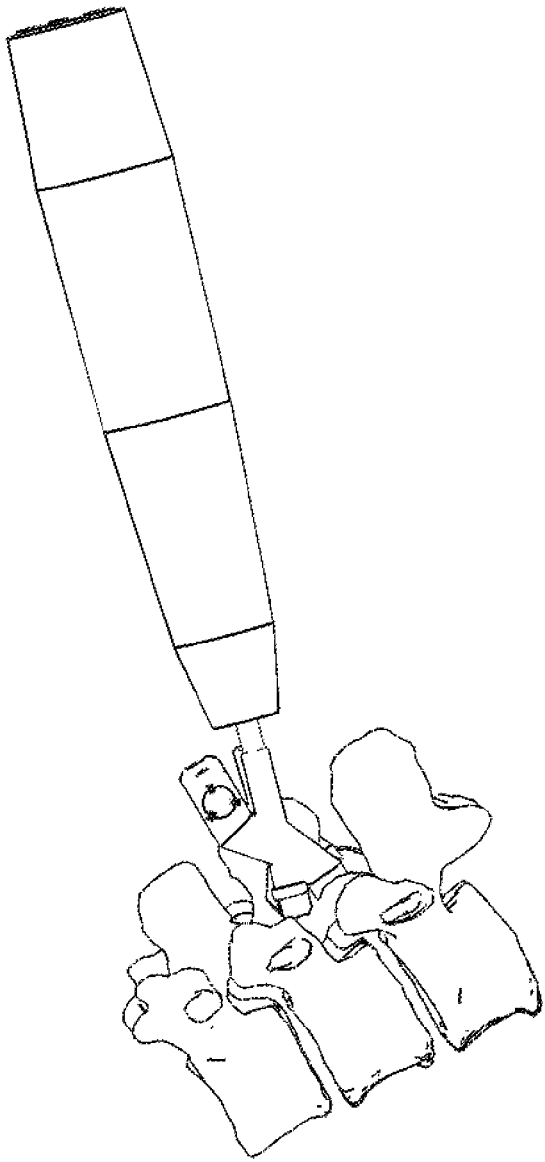
FIGS. 17-18 show alternate views of the drilling apparatus depicted in FIG. 16.
Figure 18:
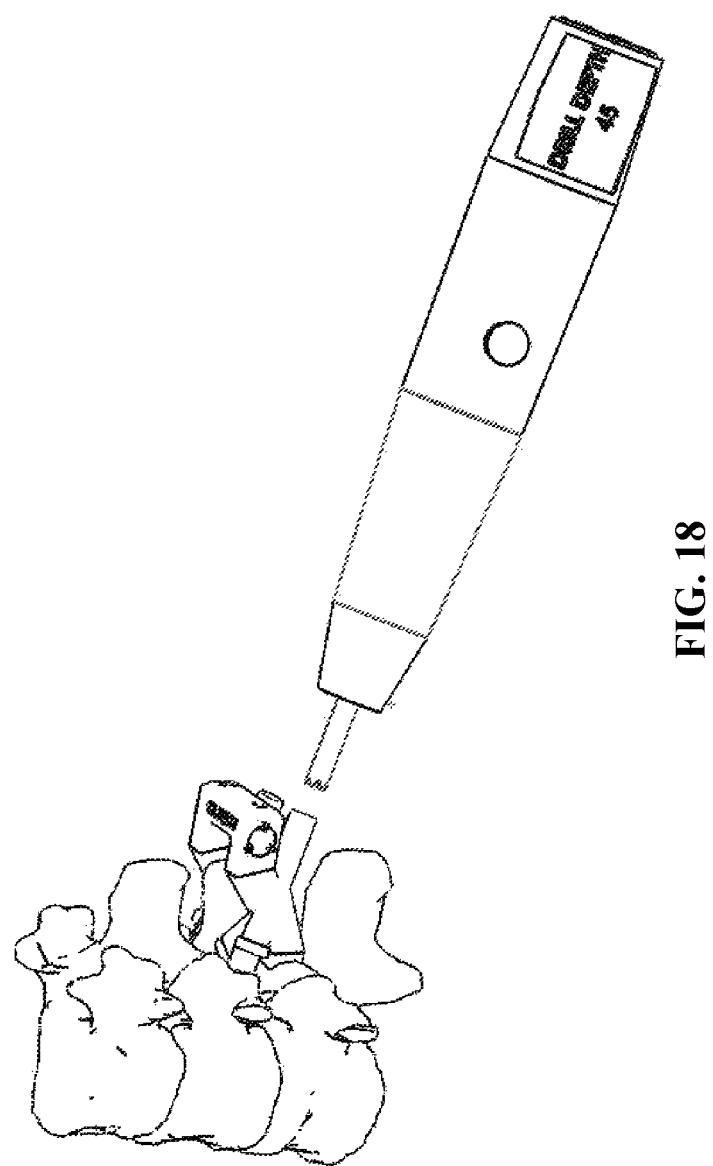

FIG. 16 shows a drilling apparatus according to another embodiment aligned with a different surgical guide. Although pedicle screw guides are the primary guide described in U.S. Pat. No. 9,642,633, the drilling apparatus may be used with a variety of bits, including drilling bits, cutting bits, and other types of blades for the desired operation. In certain embodiments the drill tip serves as an instrument sleeve and is inserted into the hollow sleeve of the guide. The tip can be removable, so that drills or other tools with different diameters may be changed to accommodate different procedures or use with different guide sizes. The sleeve protects the plastic guide from the drill bit to minimize debris left in the patient. The drill tip features a trephined tip for securely sitting on the bone surface. The tip may be removed and a smooth attachment may be inserted for use with a drill guide if the trephined tip is not required. Guides may vary as well based on the surgical procedure to be performed, including PSG, MNG, and osteotomy Guides. In FIG. 16, the guide shown is a MNG guide that has at least one hollow sleeve for receiving the drill bit or the drill chuck, as described above in relation to FIGS. 7 and 10. Different styles of guides, including laminectomy, osteotomy and other cutting guides, are contemplated for use with the drilling apparatus of the present disclosure. FIGS. 17-18 show alternate views of the drilling apparatus depicted in FIG. 16. As with the previous embodiments, the drill apparatus may be pre-programmed to include a controlled depth using the surgical guide to prevent improper use.

Figure 19:
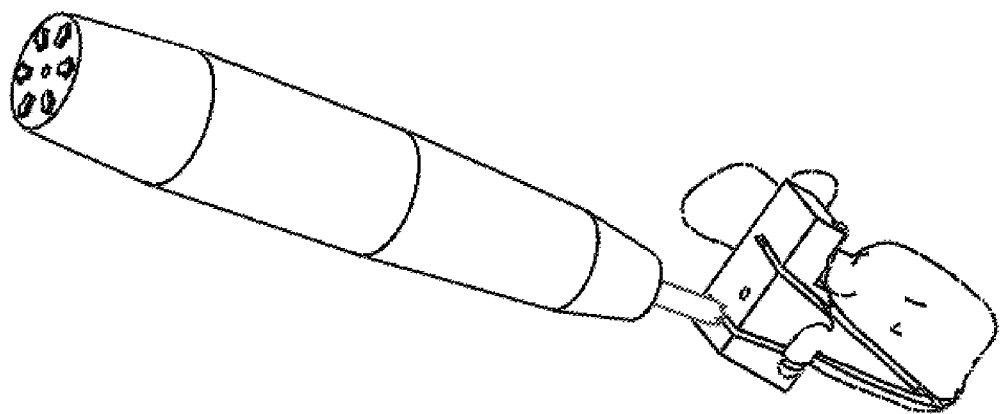
FIG. 19 shows a drilling apparatus according to another embodiment aligned with a surgical cutting guide.

FIG. 19 shows a drilling apparatus according to another embodiment aligned with an osteotomy guide. In this embodiment, a cutting blade may be connected to the chuck of the drilling apparatus for cutting a path aligned with the path of the osteotomy guide. The guide may comprise one or multiple paths for guiding the blade of the apparatus. In a preferred embodiment, the guides may only permit the blade but not the chuck to enter the paths of the guide. In an alternate embodiment, the guide may permit both the blade and the chuck to enter the paths of the guide.

Figure 20:
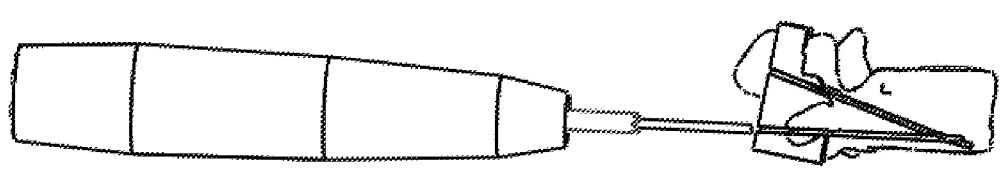
FIG. 20 shows the apparatus of FIG. 19 with a cutting tool coupled to the apparatus for use with the surgical cutting guide of FIG. 19.
Figure 21:
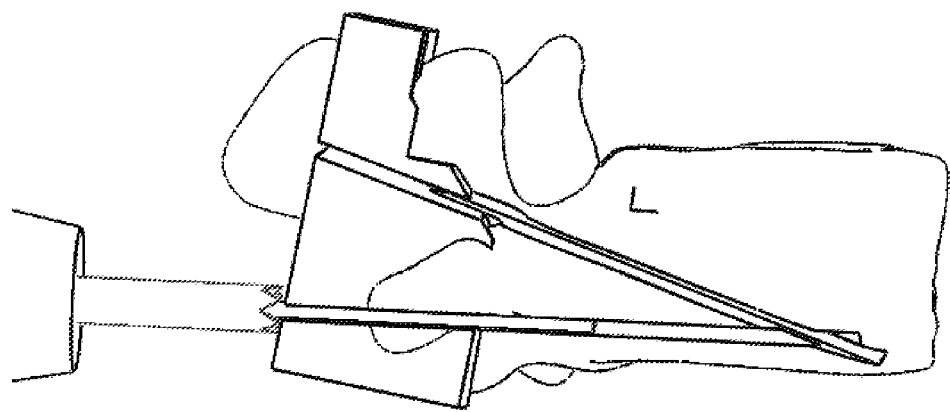
FIG. 21 is a detailed and partial sectional view of the apparatus of FIG. 20.
Figure 22:
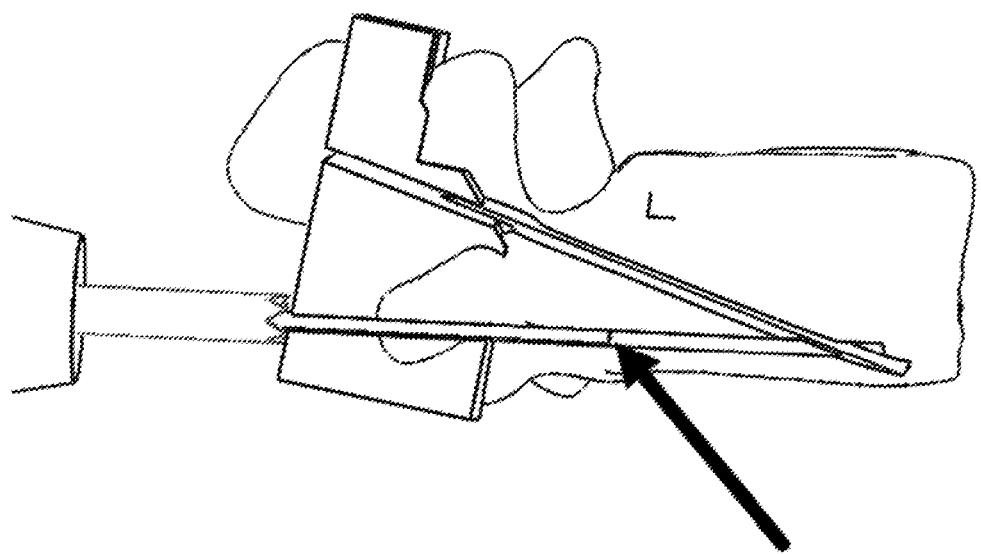
FIG. 22 is another detailed and partial sectional view showing the apparatus of FIG. 20 with the cutting tool inserted through the cutting guide of FIG. 20.

FIG. 20 shows the apparatus of FIG. 19 with a cutting tool or blade coupled to the apparatus. Here, the blade is sized to be received within the path of the osteotomy guide, and only to the depth permitted by the guide. The guide has narrow paths so that the blade may not vary from the desired trajectory, or else it will contact the surface of the guide. In certain embodiments, the drilling apparatus may be configured to sense the increased resistance of the blade hitting the wall of the guide and suspend operation of the drilling apparatus. The second path may also receive the blade of the drilling apparatus. FIGS. 21-22 are detailed and partial sectional views of the apparatus of FIG. 20.

In certain embodiments, the drill can function to protect patient anatomy and minimize buildup of heat during operation. For example, as the drill bit extends from the drill body it can sense resistance in the material it is drilling and enter a bump cycle where the drill bit extends and retracts while rotating to safely pierce and minimize heat buildup at the cortical shell of the bone. Once the cortical shell is completely drilled the bit continuously extends to the programmed depth and then retracts into the drill body. The drill then resets and the computer changes to the next programmed depth or the operator can select a new depth.

Figure 23:
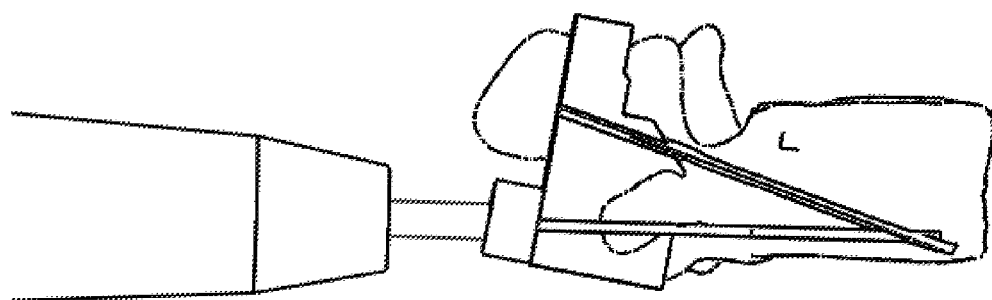
FIG. 23 shows the drilling apparatus according to another embodiment where the apparatus if aligned with a cutting guide comprising one or more sensors.
Figure 24:
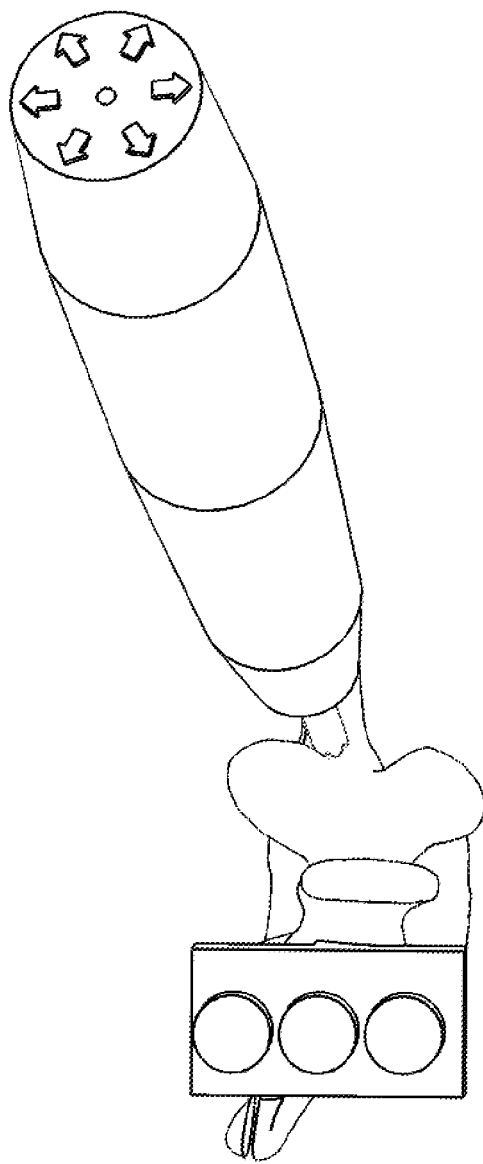
FIG. 24 shows a perspective view of the apparatus and guide of FIG. 23.

FIG. 23 shows the drilling apparatus according to another embodiment where the apparatus if aligned with a cutting guide comprising one or more sensors. The drill reads a drill depth based on the sensor reading, where the sensor is embedded in the body of the guide. The sensor may be programmed and then embedded into the guide during manufacturing, or may be a preconfigured sensor to detect the presence of the tip of the drilling apparatus based on proximity to the sensor. During operation, the drill may detect the sensor and is then proceed to operate. The guide may comprise additional sensors to detect if the tip of the apparatus is approaching a dangerous area or at risk of over-penetrating. FIG. 24 shows a perspective view of the apparatus and guide of FIG. 23.

Figure 25:
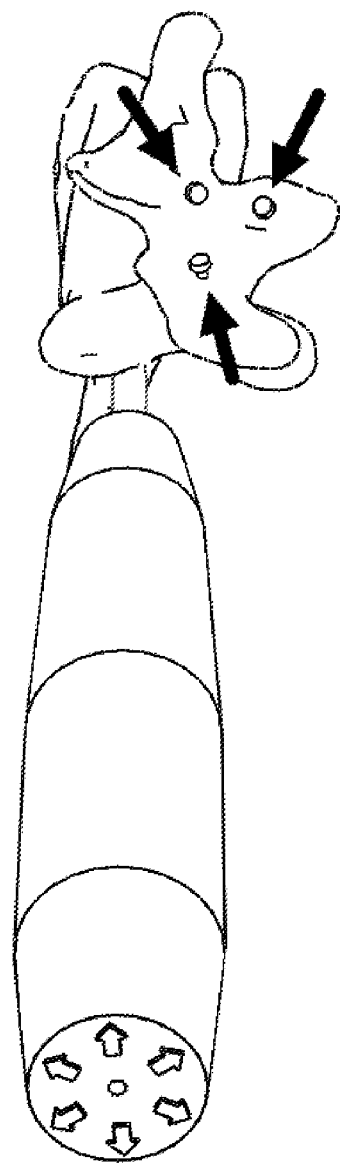
FIGS. 25-26 show the drilling apparatus and one or more sensors according to an alternate embodiment.
Figure 26:
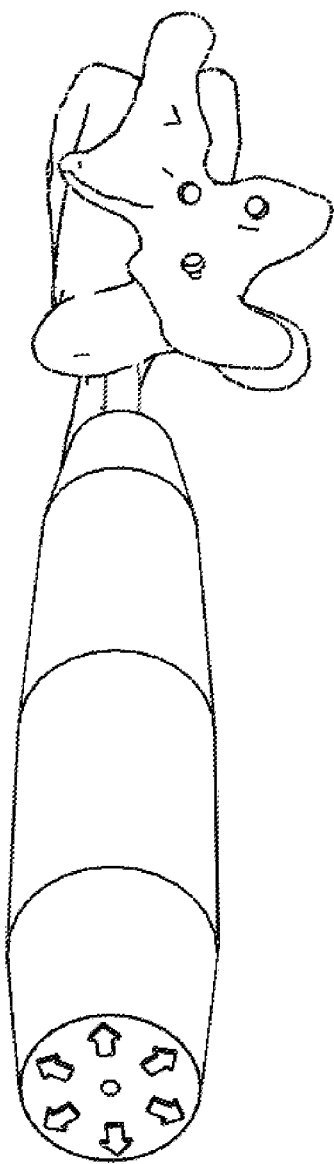

FIGS. 25-26 show the drilling apparatus and one or more sensors according to an alternate embodiment. The drill may be used with sensors placed on the patient's body to determine correct angle/trajectory based on pre-surgical planning. Sensors may be placed on the vertebra/lamina/pedicles or on a piece of plastic or other carrier that fits on the patient's anatomy (in positions determined during pre-surgical planning). The sensors communicate with the drill and locate where it is in 3D space based on pre-surgical planning measurements or from the 3D segmentation of the preoperative CT scan. The computer module in the drill (or a separate computer) may instruct an operator how to orient the drill relative to the patient's anatomy and entry point. Alternatively, the indicia on the drill may illuminate, send audible signals or otherwise inform the user when the drill is out of preferred or required alignment, and may further indicate the direction the drill should be pivoted, rotated or positioned to achieve the desired trajectory of the drill bit.

When the drill is in the correct position, it unlocks and allows the surgeon to drill to the preprogrammed depth. The lock mechanism is an internal feature of the drill that keeps the assembly from moving axially to extend the drill bit. This may be a collar, sliding pin or lock ring that can also be manually overridden by button/switch on the external part of the drill body. To unlock, the drill must be located at the correct entry point location and positioned correctly in the sagittal and transverse planes relative to the vertebral body. By creating patient specific guides or patient matched plastic blocks embedded with sensors, the drill can triangulate its position relative to the adjacent sensors and give feedback to the operator on correct placement and trajectory of the drill. Once the correct entry point position and trajectory are found, the drill unlocks and the drilling feature can be activated.

Sensors can be planned for positions on the same vertebral level in ideal location for a minimally invasive procedure such that it does not dissect past the facet capsules of the vertebra. If the drill gets off the planned trajectory it will automatically stop drilling and retract into the drill body and wait for the surgeon to realign the drill. Once the trajectory is drilled, the sensors are removed and placed on the next level, or they are left on the same level if the anatomy is fused.

The drill can also feature a barcode, radio frequency identification device ("RFID") or quick response ("QR") code reader that reads a code printed on the guide, so that pre-loading of the surgical plan or depth is not required. The code or ID be can read by the reader and relayed to the processor in real time. In a preferred embodiment, the scanner on the drill scans the code on the guide and sets the drill depth on the drill. The drill can then be used to drill that level to the correct depth without having to load data onto the drill or preprogram the depths.

The surgical guides and cutting guides described herein may be manufactured via additive manufacturing. In the context of spinal implants, the surgical guides may be used in all approaches (anterior, direct lateral, transforaminal, posterior, posterior lateral, direct lateral posterior, etc). Specific features of the surgical guides described herein can address certain surgical objectives, for example restoring lordosis, restoring disc height, restoring sagittal or coronal balance, etc.

Methods for using the apparatus are also disclosed, including methods that include a test or setup step where the operator uses the drill apparatus as described above, but also drills an initial hole at a selected trajectory. Next, the operator takes the drill bit and disconnects it from drill. Next, the operator takes a fluoroscopy shot to confirm the trajectory, and then reattaches the drill bit and drills to the programmed depth.

The surgical and cutting guides described herein may then be fabricated by any method. Fabrication methods may comprise the use of a rapid prototyping machine, a 3D printing machine, a stereolithography (STL) machine, selective laser sintering (SLS) machine, or a fused deposition modeling (FDM) machine, direct metal laser sintering (DMLS), electron beam melting (EBM) machine, or other additive manufacturing machine.

According to an alternative embodiment, anatomical data may be obtained from an ultrasonic or nuclear medicine scanning device. In yet another alternative embodiment, the data may be supplemented or merged with data from a bone density scanner to fabricate a device that is designed to remain in the patient after the surgical procedure is completed, or alternatively to achieve further control over the orientation of any desired axes, particularly where the surgical procedure involves insertion of one or more implantable devices.

One having skill in the art will appreciate that embodiments of the present disclosure may have various sizes. The sizes of the various elements of embodiments of the present disclosure may be sized based on various factors including, for example, the anatomy of the patient, the person or other device operating with or otherwise using the apparatus, the surgical site location, physical features of the devices and instruments used with the apparatus described herein, including, for example, width, length and thickness, and the size of the surgical apparatus.

One having skill in the art will appreciate that embodiments of the present disclosure may be constructed of materials known to provide, or predictably manufactured to provide the various aspects of the present disclosure. These materials may include, for example, stainless steel, titanium alloy, aluminum alloy, chromium alloy, and other metals or metal alloys. These materials may also include, for example, PEEK, carbon fiber, ABS plastic, polyurethane, polyethylene, photo-polymers, resins, particularly fiber-encased resinous materials rubber, latex, synthetic rubber, synthetic materials, polymers, and natural materials.

One having skill in the art will appreciate that embodiments of the present disclosure may be used in conjunction devices that employ automated or semi-automated manipulation. Various apparatus and implants described herein may be provided to facilitate or control the entry point, angular trajectory, height, and/or head orientation of a screw, for example. For example, the drill may include further attachments to use with taps, burrs, trials or other surgical tools and instruments.

Additional benefits of the systems and methods described herein include improving device fixation, and/or preventing unwanted contact between devices and patient anatomy (e.g. the patient's spinal cord). The further use of methods described above, including the use of software analytics, may further aid in determining screw placement and orientation to achieve the ideal screw placement and/or rod shape. For example, the use of various apparatus described herein to achieve desired screw placement and orientation in turn provides improved alignment of a secondary device, such as a rod, with the screws heads. This benefit in turn allows the surgeon/user to achieve optimal sagittal and/or coronal alignment, which assists in rod placement and improves correction of the patient's anatomy.

While various embodiments of the present disclosure have been described in detail, it is apparent that modifications and alterations of those embodiments will occur to those skilled in the art. However, it is to be expressly understood that such modifications and alterations are within the scope and spirit of the present disclosure, as set forth in the following claims. For further illustration, the information and materials supplied with the provisional and non-provisional patent applications from which this application claims priority are expressly made a part of this disclosure and incorporated by reference herein in their entirety.

It is expressly understood that where the term "patient" has been used to describe the various embodiments of the disclosure, the term should not be construed as limiting in any way. For instance, a patient could be either a human patient or an animal patient, and the apparatus and methods described herein apply equally to veterinary science as they would to surgical procedures performed on human anatomy. The apparatus and methods described herein therefore have application beyond surgical procedures used by spinal surgeons, and the concepts may be applied to other types of "patients" and procedures without departing from the spirit of the present disclosure.

The foregoing discussion of the disclosure has been presented for purposes of illustration and description. The foregoing is not intended to limit the disclosure to the form or forms disclosed herein. In the foregoing Detailed Description for example, various features of the disclosure are grouped together in one or more embodiments for the purpose of streamlining the disclosure. This method of disclosure is not to be interpreted as reflecting an intention that the claimed disclosure requires more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate preferred embodiment of the disclosure.

The present inventions, in various embodiments, include components, methods, processes, systems and/or apparatuses substantially as depicted and described herein, including various embodiments, subcombinations, and subsets thereof. Those of skill in the art will understand how to make and use the present inventions after understanding the present disclosure. The present inventions, in various embodiments, include providing devices and processes in the absence of items not depicted and/or described herein or in various embodiments hereof, including in the absence of such items as may have been used in previous devices or processes, e.g., for improving performance, achieving ease and\or reducing cost of implementation.

Moreover, though the present disclosure has included description of one or more embodiments and certain variations and modifications, other variations and modifications are within the scope of the disclosure, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A drill for use in a surgical setting, comprising:
   a body;
   a processor, the processor comprising non-transitory memory and configured to operate via computational machinery;
   a bit;
   a motor;
   a display located on the body and capable of displaying information to the operator of the drill;
   a port for accepting amemory storage device;
   at least one of a sensor or scanner;
   wherein the bit is movable, relative to the body, between a first position and a second position, wherein the processor is configured to receive information from the non-transitory memory to provide instructions for operating the motor to move the drill bit from the first position to the second position, wherein the at least one of a sensor or scanner is configured to read information and communicate with the processor to provide at least the second position; and
   wherein the drill further comprises a plurality of indicia on the proximal end of the body and in communication with the processor, the indicia configured to provide directional information to the operator while the drill is in use.

2. The drill according to claim 1 further comprising a chuck configured to receive one or more of a bit, blade, cutting tool, burr, tab and trial.

3. The drill according to claim 1 wherein the scanner is configured to read one or more of a barcode, RFID device or QR code located on an external instrument, guide or device, and wherein the information stored on the barcode, RFID device or QR code comprises at least the type of instrument, guide or device.

4. The drill according to claim 3 wherein the drill is configured to be used with a surgical guide having at least one hollow sleeve configured to receive one of the bit and the body of the drill.

5. The drill according to claim 1 wherein the processor obtains information from at least one sensor or scanner to determine the location of the bit relative to a desired location and communicates the information to the plurality of indicia.

6. The drill according to claim 5 wherein the indicia further comprise an audible alert when the drill is positioned in an undesirable position.

7. The drill according to claim 1 wherein the at least one sensor or scanner comprises a sensor positioned on a landmark for navigating the bit of the guide relative to the landmark.

8. The drill according to claim 1 wherein the memory storage device comprises instructions, which are received in the non-transitory memory of the processor of the drill and provide specific operations for the drill.

9. The drill according to claim 8 wherein the processor is capable of suspending or terminating operation of the drill when the bit of the drill deviates from the specific operations for the drill obtained from the instructions.

10. The drill according to claim 1 wherein the drill comprises a scanner configured to read a barcode, RFID device or QR code located on a surgical guide to determine the second position.

11. The drill according to claim 1 wherein the display is configured to show the first position and the second position and while the drill is in operation update the value of the second position.

12. The drill according to claim 1 wherein the display is configured to display an initial programmed position of the bit and an actual position of the bit while the drill is in operation.

13. The drill according to claim 1 wherein the non-transitory memory is configured to store more than one program and provide instructions to the drill for performing more than one operation relative to a surgical guide associated with the more than one operation.

14. The drill according to claim 13 wherein the guide is manufactured by a rapid prototyping machine, a 3D printing machine, a stereolithography (STL) machine, a selective laser sintering (SLS) machine, a fused deposition modeling (FDM) machine, a direct metal laser sintering (DMLS) machine, an electron beam melting (EBM) machine, or an additive manufacturing machine.

15. The drill according to claim 14 wherein the guide comprises at least one patient-specific contacting surface corresponding to a unique anatomical landmark of a patient.

16. The drill according to claim 1 wherein the processor is capable of obtaining instructions to require the drill to become registered relative to the at least one sensor or scanner before the drill operation is permitted to commence.

17. A drill for use in a surgical setting,
   comprising:
   a body;
   a processor, the processor comprising non-transitory memory and configured to operate via computational machinery;
   a bit;
   a motor;
   a display located on the body and capable of displaying information to the operator of the drill;
   at least one of a sensor or scanner;
   wherein the bit is movable, relative to the body, between a first position and a second position, wherein the processor is configured to receive information from the non-transitory memory to provide instructions for operating the motor to move the drill bit from the first position to the second position, wherein the at least one of a sensor or scanner is configured to read information and communicate with the processor to provide at least the second position; and wherein the drill further comprises a plurality of indicia on the proximal end of the body and in communication with the processor.

18. The drill of claim 17, wherein the indicia are configured to provide directional information to the operator while the drill is in use.

\* \* \* \* \*